US010631755B2

(12) United States Patent
Boden, Jr.

(10) Patent No.: US 10,631,755 B2
(45) Date of Patent: Apr. 28, 2020

(54) DETECTION OF SPATIAL LOCATION AND ROTATION OF A PROGRAMMABLE IMPLANTABLE VALVE

(71) Applicant: Integra LifeSciences Switzerland Sárl, Le Locle (CH)

(72) Inventor: Thomas Boden, Jr., Middleboro, MA (US)

(73) Assignee: Integra LifeSciences Switzerland Sarl, Le Locle (CH)

( * ) Notice: Subject to any disclaimer, the term of this patent is extended or adjusted under 35 U.S.C. 154(b) by 579 days.

(21) Appl. No.: 15/399,549

(22) Filed: Jan. 5, 2017

(65) Prior Publication Data
US 2018/0184943 A1    Jul. 5, 2018

(51) Int. Cl.
*A61B 5/06*    (2006.01)
*A61M 27/00*    (2006.01)

(52) U.S. Cl.
CPC ........... *A61B 5/062* (2013.01); *A61M 27/006* (2013.01); *A61B 2562/0223* (2013.01)

(58) Field of Classification Search
CPC ........... A61B 5/06; A61B 5/062; A61B 5/064; A61B 5/065; A61B 2562/02; A61B 2562/0223; A61B 2562/04; A61B 2562/06; A61B 2562/08; A61M 27/002; A61M 27/006
USPC ........ 600/407, 424–426, 431; 623/1.24, 1.34
See application file for complete search history.

(56) References Cited

U.S. PATENT DOCUMENTS

| | | | |
|---|---|---|---|
| 4,595,390 A | 6/1986 | Hakim et al. | |
| 5,879,297 A | 3/1999 | Haynor et al. | |
| 6,129,668 A | 10/2000 | Haynor et al. | |
| 6,263,230 B1 | 7/2001 | Haynor et al. | |
| 6,391,019 B1 | 5/2002 | Ito | |
| 6,439,538 B1 | 8/2002 | Ito | |
| 6,485,449 B2 | 11/2002 | Ito | |
| 6,702,249 B2 | 3/2004 | Ito | |
| 7,334,582 B2 * | 2/2008 | Bertrand | A61M 27/006 128/899 |
| 7,856,987 B2 * | 12/2010 | Bertrand | A61M 27/006 128/899 |
| 8,015,977 B2 | 9/2011 | Bertrand et al. | |
| 8,257,296 B2 | 9/2012 | Bertrand et al. | |

(Continued)

*Primary Examiner* — Ahmed M Farah
(74) *Attorney, Agent, or Firm* — Cohen & Hildebrand, PLLC

(57) ABSTRACT

Detecting spatial location and rotation (pitch, roll and yaw) of an implantable programmable valve device having a direction of flow of fluid therethrough. A permanent-magnet rotor disk associated with the valve has magnets arranged in a ring. A single position within the ring represents a moveable reference marker position. Also included in the valve is a first fixed, stationary, non-moveable magnet disposed a predetermined distance relative to the moveable reference marker position. A magnetoresistive sensor array produces the asymmetric magnetic field pattern including a moveable reference marker corresponding to the moveable reference marker position in the ring and a first fixed reference marker corresponding to the first fixed, stationary, non-moveable magnet. An indicator device determines spatial location based only on the moveable reference marker and yaw based on the moveable reference marker relative to the first fixed reference marker.

18 Claims, 11 Drawing Sheets

(56) References Cited

U.S. PATENT DOCUMENTS

| | | | |
|---|---|---|---|
| 8,539,956 B2 | 9/2013 | Bertrand et al. | |
| 8,622,978 B2 | 1/2014 | Bertrand et al. | |
| 8,630,695 B2 * | 1/2014 | Negre | A61B 5/06 |
| | | | 128/899 |
| 10,518,069 B2 * | 12/2019 | Boden, Jr. | A61M 27/006 |
| 2014/0121586 A1 | 5/2014 | Bertrand et al. | |
| 2014/0336560 A1 * | 11/2014 | Hakim | A61M 27/006 |
| | | | 604/9 |
| 2018/0015266 A1 * | 1/2018 | Amery | G01D 7/00 |
| 2019/0083763 A1 * | 3/2019 | Boden, Jr. | G01R 33/0076 |
| 2019/0083764 A1 * | 3/2019 | Boden, Jr. | A61M 27/006 |

* cited by examiner

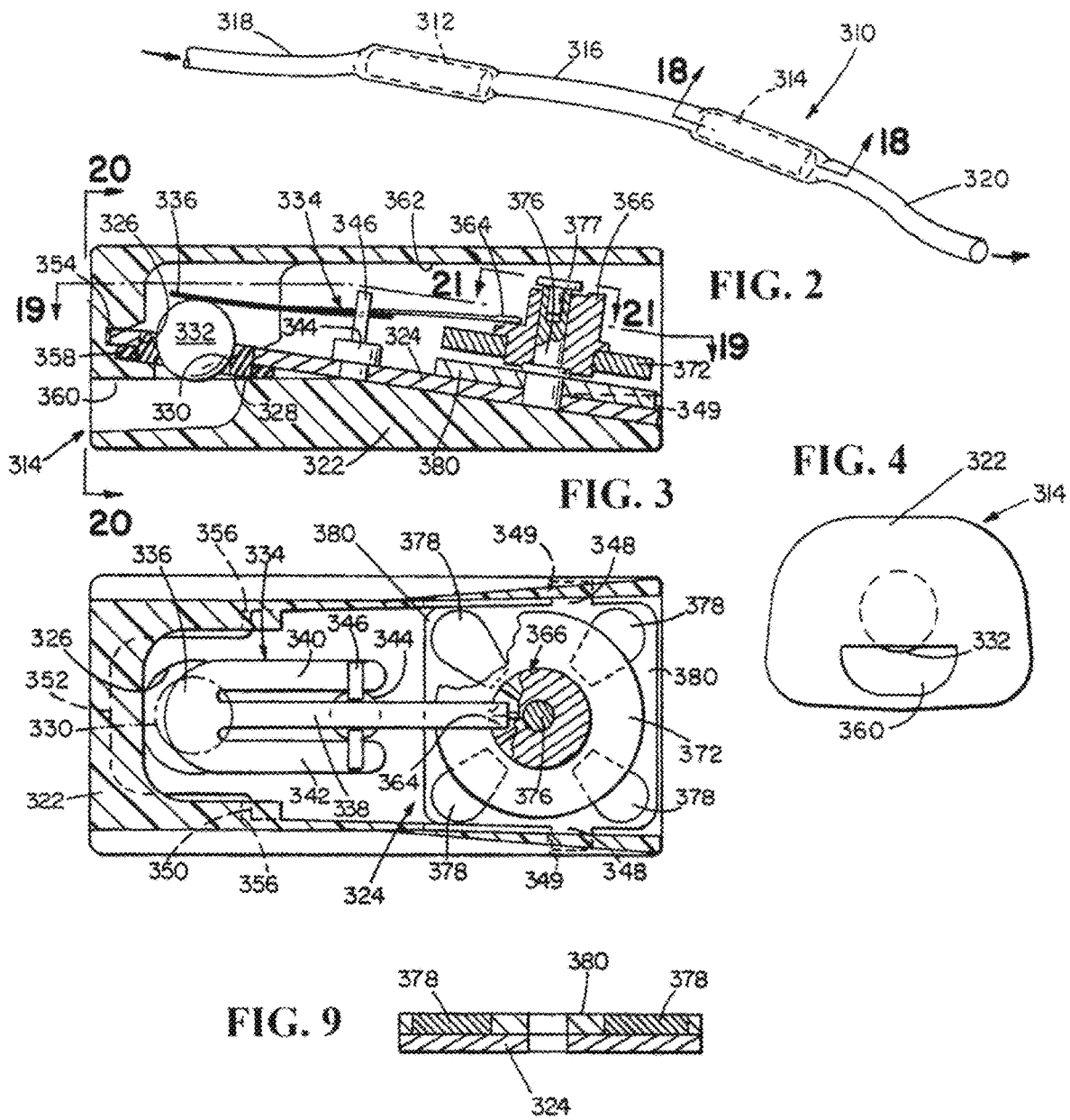

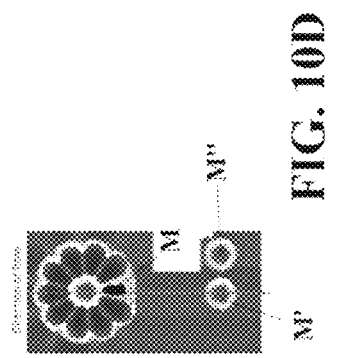

DETECTION OF SPATIAL LOCATION AND ROTATION OF A PROGRAMMABLE IMPLANTABLE VALVE

BACKGROUND OF THE INVENTION

Field of the Invention

The present invention relates to a system and method for controlling an implantable valve for drainage of a bodily fluid. In particular, a system and method using magnets to detect spatial location and rotation (pitch, roll and yaw) of a programmable implantable hydrocephalus valve for drainage of cerebral spinal fluid.

Description of Related Art

Hydrocephalus is the accumulation of cerebrospinal fluid in the brain, resulting from increased production, or more commonly, pathway obstruction or decreased absorption of the fluid. Cerebrospinal fluid (CSF) shunts have been used for decades for the treatment of hydrocephalus. A CSF shunt involves establishing an accessory pathway for the movement of CSF to bypass an obstruction of the natural pathways.

The shunt is positioned to enable the CSF to be drained from the cerebral ventricles or sub-arachnoid spaces into another absorption site (e.g., the right atrium of the heart or the peritoneal cavity) through a system of small catheters. A regulatory device, such as a valve, may be inserted into the pathway of the catheters. In general, the valve keeps the CSF flowing away from the brain and moderates the pressure or flow rate. The drainage system using catheters and valves enables the excess CSF within the brain to be evacuated and, thereby, the pressure within the cranium to be reduced.

Some implantable valves are fixed pressure valves (i.e., monopressure valves) while others have adjustable or programmable settings. Programmable or adjustable implantable valves are desirable in that the valve pressure setting may be varied non-invasively via an external control device over the course of treatment without requiring explantation. One such conventional adjustable or programmable implantable valve is the Codmin-Hakim-Programmable Valve (CHPV), as disclosed in U.S. Pat. No. 4,595,390, which is assigned to DePuy Orthopedics, a J&J company related to that of the present assignee, and herein incorporated by reference in its entirety.

Before a current parameter setting may be verified and/or one or more parameter settings of an implantable valve may be adjusted or changed via an external control device, the spatial location of the implantable medical device (e.g., the implantable programmable valve) has to be detected or located. Heretofore, the implantable valve device has been detected by manipulation and touch by medical personnel and/or x-ray imaging that identifies a radiopaque marker on the implantable device.

Once the implantable valve has been located, one or more external devices may be used to detect the current parameter setting (e.g., current "popping" pressure setting of the valve) and/or vary a parameter setting (e.g., new pressure setting of the valve) associated with the implantable valve. The proper reading of either the current parameter setting or adjustment to a new parameter setting first requires proper detection of spatial location (identification of the center of the adjustment mechanism) as well as rotation (pitch, roll and yaw) of the implantable medical device. Manual manipulation alone is imprecise in determining the spatial location (identification of the center of the adjustment mechanism) and rotation of the implantable medical device. X-ray imaging is more precise in determining these attributes, however, repeated exposure to x-ray imaging has undesirable health implications.

It is therefore desirable to develop a system and method that alleviates the problems associated with conventional programmable implantable valves in which the spatial location as well as the rotation (pitch, roll and yaw) of the programmable implantable valve may be precisely detected without requiring x-ray imaging.

SUMMARY OF THE INVENTION

An aspect of the present invention is directed to an improved system and method for detecting the spatial location (identification of the center of the adjustment mechanism) as well as rotation (pitch, roll and yaw) of an implantable programmable valve without requiring x-ray imaging or manual manipulation.

Another aspect of the present invention is directed to an, improved system and method for determining the spatial location as well as rotation (pitch, roll and yaw) of an implantable programmable valve using a plurality of magnetic reference markers associated with the implantable valve device.

The present invention is directed to a system for detecting spatial location as well as rotation including pitch, roll and yaw of an implantable programmable valve device having a direction of flow of fluid therethrough. The system includes a permanent-magnet rotor disk associated with the implantable programmable valve and having a plurality of three or more magnets arranged in a ring. A single position within the ring represents a moveable reference marker position. The implantable programmable valve also includes a first fixed, stationary, non-moveable magnet associated with the implantable programmable valve and disposed a predetermined distance relative to the moveable reference marker position. The system further includes a two-dimensional array of 3-axis magnetoresistive sensors for detecting the asymmetric magnetic field pattern including a moveable reference marker corresponding to the moveable reference marker position in the ring and a first fixed reference marker corresponding to the first fixed, stationary, non-moveable magnet. An indicator device determines spatial location based only on the moveable reference marker and yaw based on the moveable reference marker relative to the first fixed reference marker.

The present invention also relates to a method for using a system for detecting the spatial location as well as rotation (pitch, roll and yaw) of an implantable programmable valve device having a direction of flow of fluid therethrough. The system includes a permanent-magnet rotor disk associated with the implantable programmable valve and having a plurality of three or more magnets arranged in a ring; wherein a single position within the ring represents a moveable reference marker position; the implantable programmable valve further comprises a first fixed, stationary, non-moveable magnet disposed a predetermined distance relative to the moveable reference marker position. The method includes the step of selecting a single position from within the ring, as the moveable reference marker position. An asymmetrical magnetic field pattern is detected using a two-dimensional array of 3-axis magnetoresistive sensors, wherein the asymmetrical magnetic field pattern includes a moveable reference marker corresponding to the moveable reference marker position among the plural magnets in the ring and a first fixed reference marker corresponding to the first, fixed, stationary, non-moveable magnet. Then an indicator device is used to determine the spatial location of the implantable programmable valve based only on the moveable reference marker and the yaw based only on the moveable reference marker relative to the first fixed reference marker.

BRIEF DESCRIPTION OF THE DRAWING

The foregoing and other features of the present invention will be more readily apparent from the following detailed description and drawings of illustrative of the invention wherein like reference numbers refer to similar elements throughout the several views and in which:

FIG. 1 is a perspective diagrammatic view of an exemplary valve assembly;

FIG. 2 is a cross-sectional view taken at 18-18 of FIG. 1;

FIG. 3 is a cross-sectional view taken at 19-19 of FIG. 2;

FIG. 4 is an elevational view taken at 20-20 in FIG. 2;

FIG. 9 is a cross-sectional view taken at 24A-24A in FIG. 8;

FIG. 10D is an exemplary magnetic field pattern detected by the two-dimensional array of 3-axis magnetoresistive sensors associated with the indicator tool for the permanent-magnet rotor disk in FIG. 10B;

DETAILED DESCRIPTION OF THE INVENTION

Figure 5:
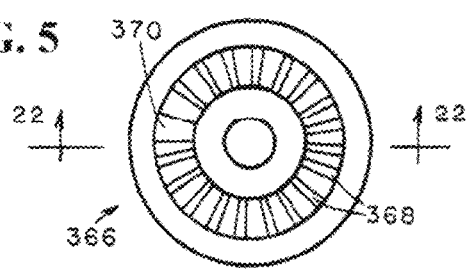
FIG. 5 is a plan view at 21-21 in FIG. 2, showing the cam of said embodiment.

The present invention is directed to a shunt valve assembly including: a programmable implantable valve 314; an external indicator device; an external valve adjustment device 390 and an external control device 396. Referring to FIG. 1, an illustrative example of a shunt valve assembly 310 with two shunt valves 312, 314 separated by a pumping chamber 316 is shown. Of course, the shunt valve assembly may be configured with only a single shunt valve 314, thereby eliminating the shunt valve 312. Cerebroventricular catheter 318 is connected to the inlet of the valve assembly, and drainage catheter 320, to the outlet. This assembly may be surgically implanted following, well-known procedures.

A cross-sectional view through the downstream shunt valve 314 is shown in FIG. 2. The upstream valve 312 is preferably the same except that the adjustment mechanism is absent. (The tubular plastic covering shown tightly fitted around the valves in FIG. 1 is not shown in the remaining figures.) Valve body 322 (preferably, injection molded from a surgically-implantable material such as polyethersulfone) has within its interior an inclined plate 324 made from a nonmagnetic material, such as titanium or stainless steel. The inclined plate 324 has circular aperture 326 in which is press fit a sapphire ring 328, with frustoconical surface 330 forming a valve seat for spherical ball 332 (e.g., highly-polished ruby).

Biasing the ball 332 against the valve seat is spring 334 (for example, a single piece of stainless steel or another suitable material), shown in plan view in FIG. 3. The spring 334 provides a relatively low K factor to produce relatively little change in working pressure with changes in flow (i.e., a flat flow-pressure curve). Spring 334 has base 336 overlying ball 332, central arm 338 extending from the base 336 to an adjustment mechanism, and two flanking arms 340, 342 extending from the base to a yoke 344. The yoke 344 is press fit into a hole in plate 324 and tabs 346 extend over the tops of the flanking arms 340, 342. Yoke 344 is relieved in the center to provide room for the central arm to pass through. Notches (not shown) cut in the ends of flanking arms 340, 342 receive portions of the yoke 344, and secure the spring 334 against longitudinal movement. Spring 334 is secured against sideward movement by contact of the flanking arms 340, 342 with the vertical outside surfaces of the yoke 344.

Figure 8:
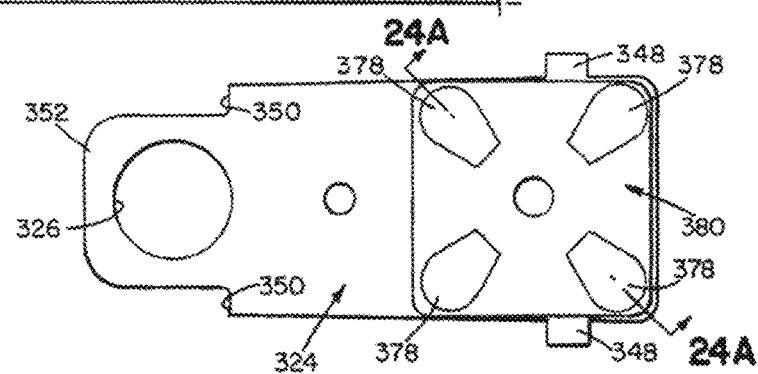
FIG. 8 is a plan view of the internal support plate.
Figure 11:
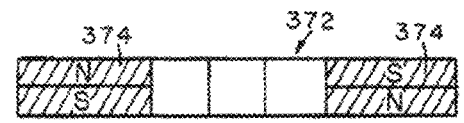
FIG. 11 is a cross-sectional view of said disk taken at 11-11 in FIG. 10A.

Plate 324 is held tightly in place within valve body 322 by sliding the plate 324 into the valve body (in a direction from right to left in FIG. 2). Grooves 354, 356 at the upstream end of the valve body 322 receive portions 350, 352 (FIG. 8) of the plate 324, and grooves 349 at the downstream end receive tabs 348 on the plate. The grooves extend generally horizontally rather than in the inclined direction followed by the plate, and thus the tabs 348 and portions 350, 352 tend to become tightly wedged into the grooves.

Grooves 354, 354 at the ball end of the valve body also serve to press plate 324 downwardly so as to squeeze it tightly against O-ring 358 (e.g., silicone rubber), which provides an internal seal to ensure that all flow through the valve is through the orifice formed between the ball 332 and the valve seat 330. Flow through the valve is from inlet cavity 360, past ball 332, and into outlet cavity 362.

Figure 6:
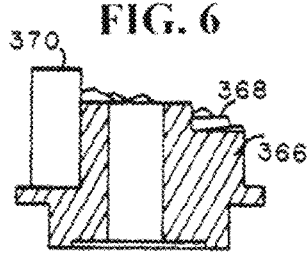
FIG. 6 is a cross-sectional view of said cam taken at 22-22 in FIG. 5.
Figure 7:
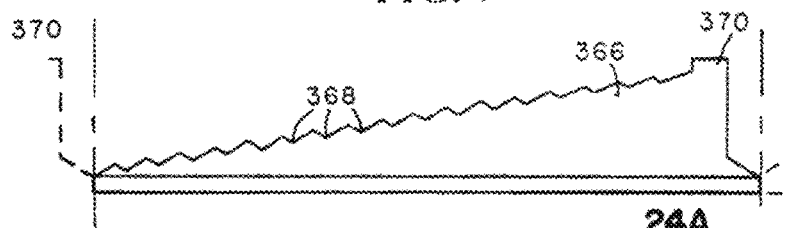
FIG. 7 is, a diagrammatic view of the steps of said cam.

The preload of spring 334 against ball 332 is adjusted by using cam 366 to vary the vertical position (preferably, through an approximate 0.75 mm range) of free end 364 of central arm 338. The spring preload establishes the pressure of the valve. The cam, as illustrated in FIGS. 5-7, is configured as a circular staircase of a plurality of steps 368 (preferably, 18 steps), each step 368 being grooved so as to have a V-shape cross section. Free end 364 of central arm 338 has a similar V-shape complementary to that of the V-shape of steps 368. At each end of the staircase of steps a barrier 370 is provided to confine rotation of the cam to slightly less than one revolution. The V-shape of steps 368 act as a series of detents to keep the cam in precisely one of a plurality (e.g., 18) of possible angular positions. As a result, in the exemplary embodiment, the vertical position of free end 364 of central arm 338 is precisely one of eighteen different values and, in turn, the working pressure of the valve is at one of eighteen possible levels. Of course, the number of steps may be modified, as desired, to have any number of two or more possible levels with the number of steps adjusted accordingly.

Cam 366 is press fit into the central hole in a rotor 372 (e.g., 4 mm diameter), with a protrusion on the cam fitting into recess 373 in the rotor to assure accurate angular positioning. The cam-rotor unit rotates loosely on shaft 376, the base of which is press fit into plate 324. The cam-rotor unit is retained by retaining element 377 secured to the top of the shaft 376. Rotor 372 is preferably made of platinum cobalt or samarium cobalt (which may be plated with platinum to improve corrosion resistance).

Figure 13:
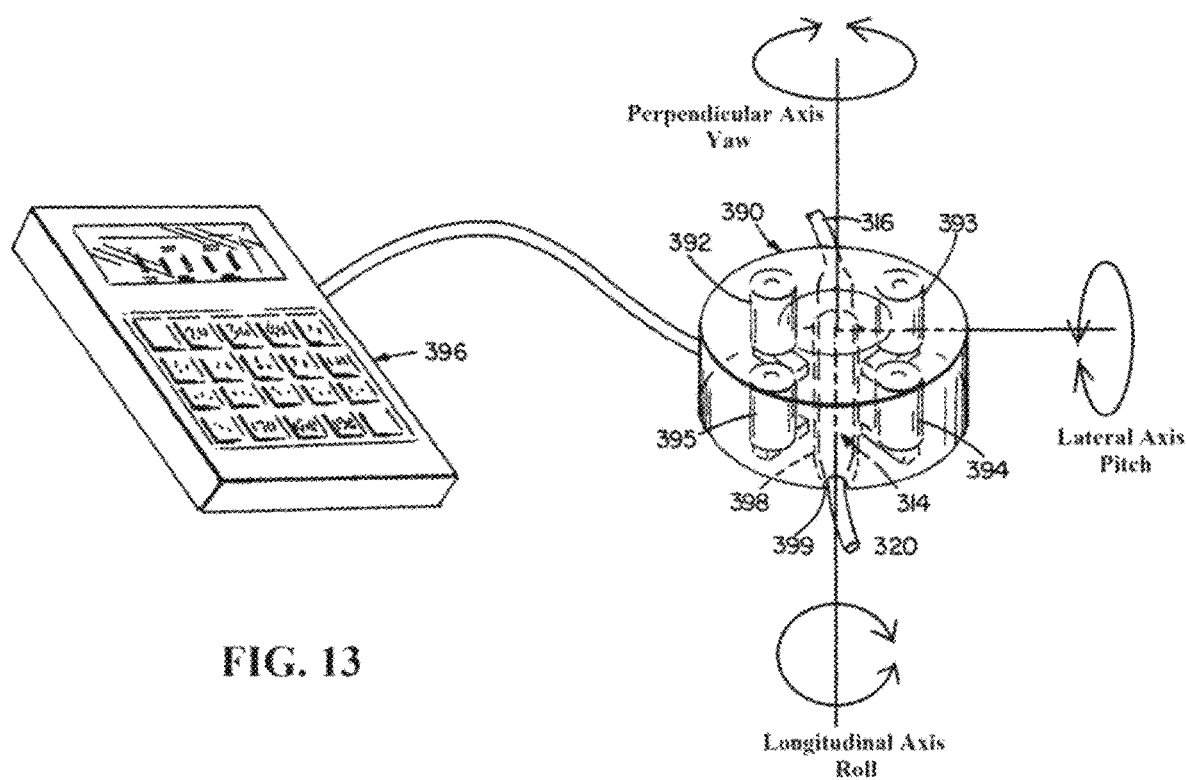
FIG. 13 is a diagrammatic view of the valve of FIG. 2 in accordance with the present invention capable of detecting pitch, roll and yaw along illustrated respective x, y and z axes.

Rotor 372 has an inventive configuration that will be now be described in detail. Specifically rotor 372 comprises a plurality of magnets formed into a circular shape ring or disk. At any one angular position within the ring or disk, the magnetic pole exposed on the top surface of the disk is, opposite that of the one exposed on the bottom surface. Depending on patient anatomy and placement location of the implantable device it may be difficult to locate the implantable device and properly orient the external magnetic indicator device over the implantable valve. The present inventive system is directed to an improved implantable valve device and corresponding external magnetic indicator device that together allow detection of the spatial location (within an x, y, z coordinate system) of the it valve device and detect any rotation (e.g., pitch, roll and/or yaw) of the implantable valve device without the need for imprecise manual manipulation and/or requiring x-ray imaging which over repeated use has deleterious impact on the patient's health. For the purposes of this invention, the terms pitch, roll and yaw represent rotation of the implantable valve device as defined relative to each of the respective three axes (x, y, z) perpendicular to one another and intersecting at right angles at the implantable programmable valve's center of gravity, as illustrated in FIG. 13. The x-axis (longitudinal axis) is arranged along the direction of flow of fluid through the valve, while the y-axis (lateral axis) is perpendicular to but in the same plane as the x-axis. The z-axis (vertical or perpendicular axis) is perpendicular to both the x-axis and y-axis, but not in the same plane as either the x or y-axes. Rotation about the x-axis is called "roll"; rotation about the y-axis is referred to as "pitch"; while rotation about the z-axis is hereinafter "yaw." Determining the spatial location and rotation of the implantable valve is useful both prior to verifying a current program setting (e.g., current valve pressure setting) and before programming a new parameter setting using an external control device.

It has been recognized by testing that if all the magnets of the same polarity in the ring of plural magnetic poles of alternating polarity on the rotor 372 are demagnetized the valve may still be properly programmed. Therefore, in a valve assembly with a rotor having, for example, 10 magnets arranged in a circular ring alternating in polarity, all 5 of the north magnets and all 5 five of the south magnets are not needed to program the valve to the desired valve pressure setting. It is based on this underlying premise that the present invention contemplates that only one of the positions within the ring of magnets on the rotor may be used as a moveable reference marker position that produces an asymmetric magnetic field pattern based on which the spatial location of the implantable valve is determined.

Figure 15:
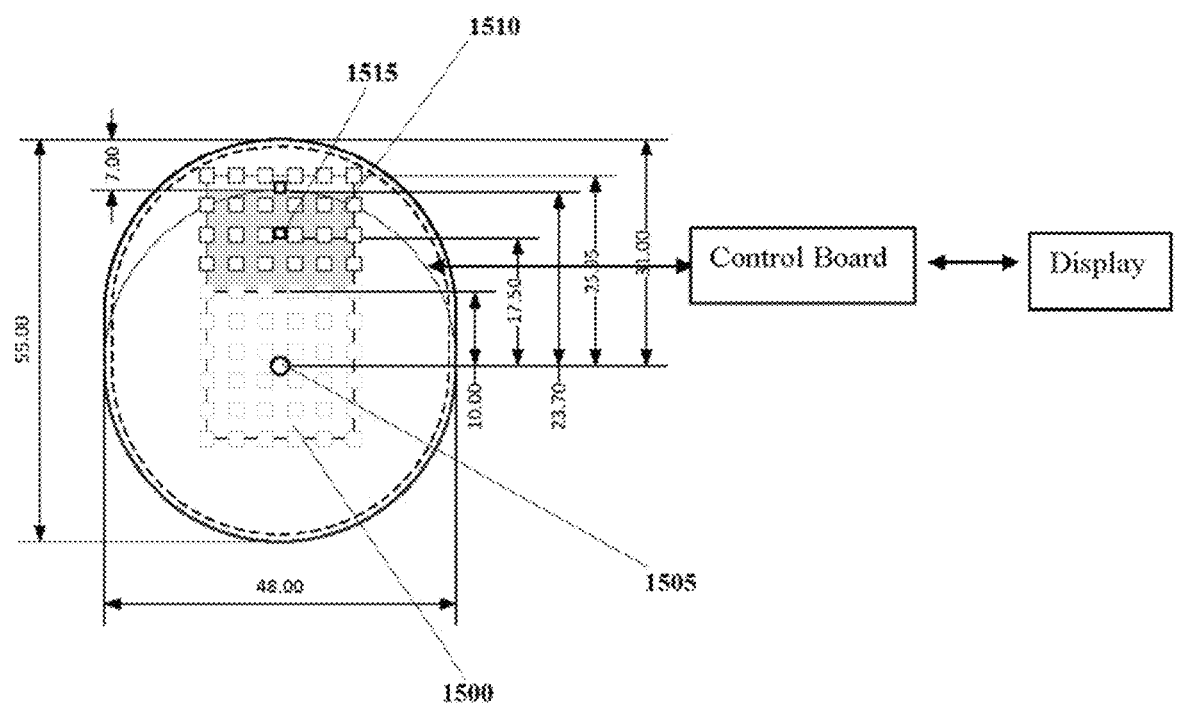
FIG. 15 is an exemplary two dimensional array of the present inventive 3-axis magnetoresistive sensors in the external indicator device to detect pitch, roll and yaw of the implantable programmable valve.

In accordance with the present invention, the rotor 372 comprises a plurality of three or more permanent magnets 374 alternating in polarity (north and south) arranged in a circular ring, wherein the magnets are selected or configured so as to produce or detect an asymmetrical magnetic field pattern by a two-dimensional array of 3-axis magnetoresistive sensors in the external indicator device, as depicted in FIG. 15.

Figure 10A:
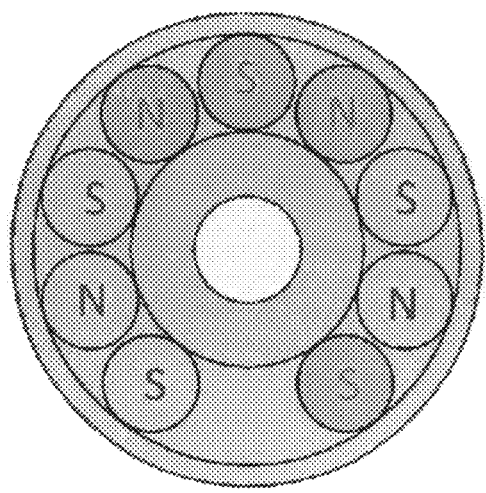
FIG. 10A is a plan view of the permanent-magnet rotor disk in accordance with the present invention having an odd number of magnets each equal in size and strength arranged in a ring, by illustrative example, 9-magnets arranged in a ring.

To produce such an asymmetrical magnetic field pattern, the rotor 372 comprises a ring of three or more permanent magnetic poles alternating in polarity and exhibiting one of several novel characteristic arrangements. Several different configurations of the rotor may produce the desired asymmetric magnetic field pattern by selecting a single moveable reference marker position from within the ring of magnets. In a first characteristic arrangement, a moveable or asymmetric reference marker position associated with the rotor is denoted by a position within the ring of plural magnets wherein a corresponding single magnet is missing or omitted from the ring. Specifically, the plurality of magnets in the ring are arranged so that the single missing or omitted magnet leaves only a single predetermined spacing displacement (D) between two adjacent magnetic poles, preferably having the same polarity. All the remaining adjacent magnets in the ring alternate in polarity and are positioned relative to one another by a substantially equidistant spacing, displacement (d). The distance (d) is less than the distance (D). This first characteristic arrangement is envisioned by configuring the rotor comprising a plurality of magnets of alternating polarity arranged in a ring, in which only one of the magnets in the ring is omitted or missing. Within the ring, the position of the omitted or missing magnet denotes or serves as the moveable reference marker that produces an asymmetrical magnetic field pattern by the external indicator device (e.g., the magnetoresistive sensor array). FIG. 10A is an illustrative example of a rotor having 96-magnets with a spacing displacement (D)>>than the distance (d). To be precise, the moveable or asymmetric reference marker is represented approximately halfway between central points associated with each of two adjacent magnets within the ring having the same polarity. Removal of one magnet of opposite polarity from the two surrounding magnets skews the blended magnetic field to create a discernible peak. That is, the magnetic flux lines from each magnet are moving N to S as they follow the path of least resistance. Having two N magnets next to one other creates a larger peak than otherwise created when a N and a S magnet are positioned next to one another.

Figure 10B:
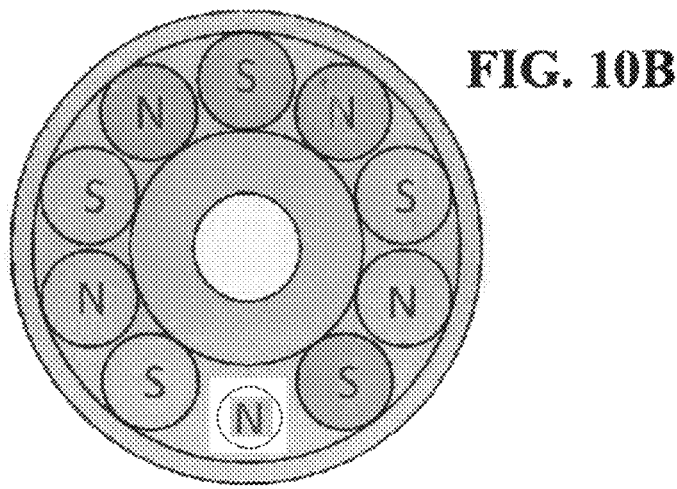
FIG. 10B is a plan view of the permanent-magnet rotor disk in accordance with the present invention having an even number of magnets arranged in a ring, by illustrative example 10-magnets arranged in a ring, wherein one of the magnets is reduced in size and/or strength relative to the other remaining magnets in the ring each of substantially equal size and/or strength.

In a second characteristic arrangement, rather than the rotor being configured to have an omitted or missing magnet, the moveable reference marker position associated with the rotor is denoted by a position of only one of the magnets in the ring reduced or enlarged in size and/or strength relative to the remaining magnets (all remaining magnets in the ring preferably being substantially equal in size and/or strength) alternating in polarity, arranged in a ring and associated with the rotor. Accordingly, only one magnet in the ring is reduced or enlarged in size and/or strength relative to that of all the remaining magnets in the ring being substantially equal in size and/or strength. FIG. 10B is an illustrative example of a rotor having 10-magnets wherein the size and/or strength of only one of the magnets in the ring is reduced relative to the remaining magnets in the ring all of substantially equal size and/or strength. Of course, the one magnet in the ring in FIG. 10B may alternatively be enlarged, rather than reduced, in size and/or strength, relative to the remaining magnets in the ring all of substantially equal size and/or strength. Once again, enlargement/reduction in size and/or strength of the single magnet in the ring skews the blended magnetic field to create a discernible peak.

Figure 10C:
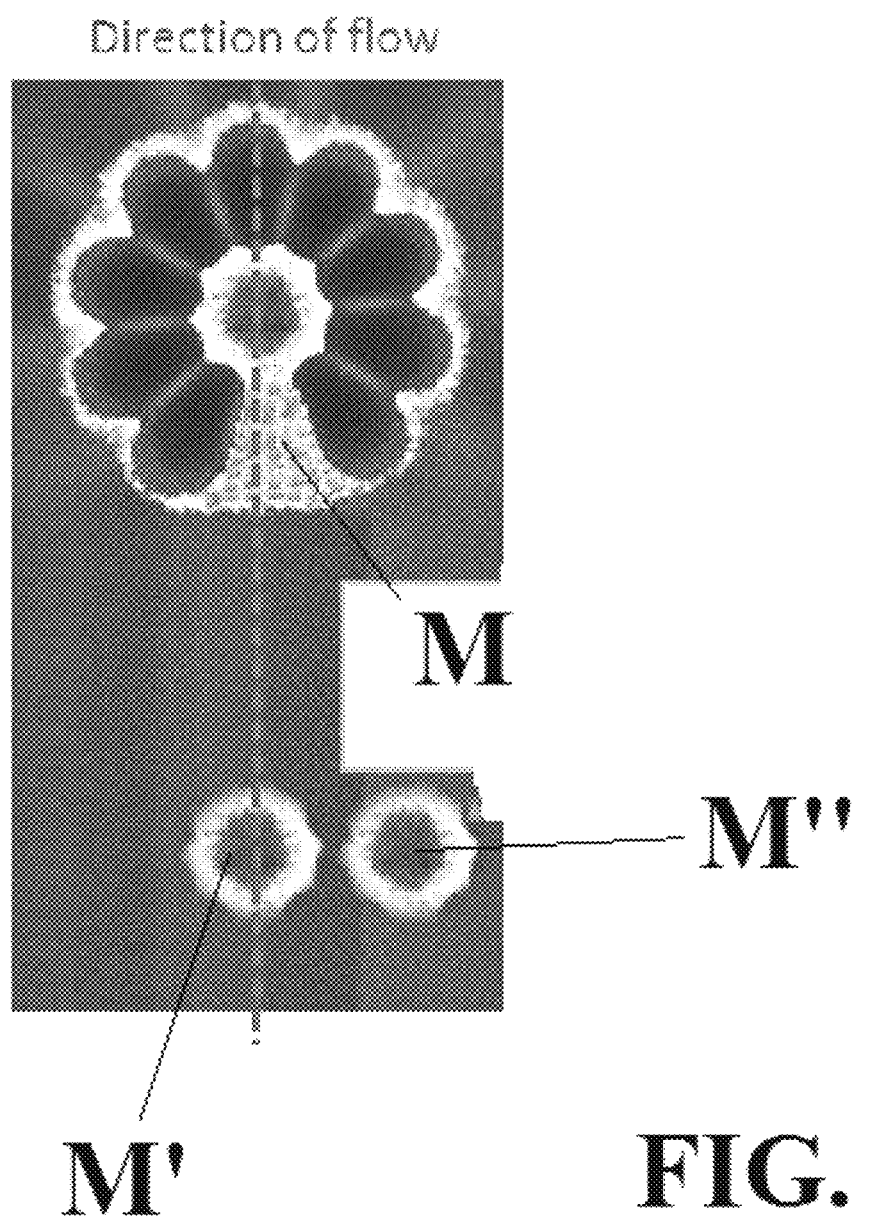
FIG. 10C is an exemplary magnetic field pattern detected by the two-dimensional array of 3-axis magnetoresistive sensors associated with the indicator tool for the permanent-magnet rotor disk in FIG. 10A.

As illustrated in FIGS. 10C and 10D, asymmetrical magnetic field patterns are produced or detected by a two dimensional array of 3-axis magnetoresistive sensors in an external indicator device (depicted in FIG. 15) based on the exemplary illustrative embodiments in FIGS. 10A & 10B, respectively. It is to, be noted that rather than being a separate device, the indicator device may be part of the valve adjustment element 390 in FIG. 3 so long as the sensor array is not so close in proximity to the coils 395 to create significant noise that would undesirably impact performance. Referring to FIG. 10C the moveable reference marker (M) is established by the substantially central position of the missing petal of the produced or detected asymmetrical magnetic field pattern associated with the position in the ring in which there is no magnet, whereas in FIG. 10D the moveable reference marker (M) produces an asymmetrical magnetic field pattern (e.g., in the shape of a single petal of a flower) whose size is reduced relative to the petals representing all other remaining magnets in the ring of substantially equal size and/or strength.

Figure 10E:
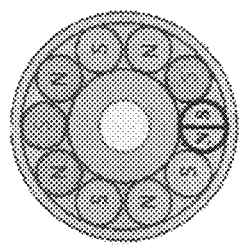
FIG. 10E is a plan view of the permanent-magnet rotor disk in accordance with the present invention, by illustrative example 10-magnets are arranged in a ring, wherein only one magnet in the ring has a 90 degree rotation in polarity relative to the remaining magnets in the ring.

Still yet, a third characteristic arrangement of the plurality of magnets associated with the rotor 372 in accordance with the present invention may be configured wherein instead of removing only one magnet in the array or reducing/enlarging the size of only one magnet in the array, rather only one magnet in the array is rotated 90 degrees relative to that of the remaining magnets in the array to intentionally skew the blended magnetic field to create a discernible peak. An exemplary configuration of such a permanent-magnet rotor disk is illustrated in FIG. 10E.

Thus, in accordance with any of the aforementioned characteristic arrangements of the plurality of magnets associated with the novel rotor 372 in accordance with the present invention, an asymmetrical magnetic field pattern is produced or detected by the two-dimensional array of 3-axis magnetoresistive sensors including a moveable reference marker corresponding to the moveable reference marker position. Irrespective of the particular characteristic arrangement of the plurality of magnets associated with the rotor, the moveable reference marker skews the blended magnetic field to create a discernible peak from which the spatial location of the implantable valve device is detected.

Figure 17:
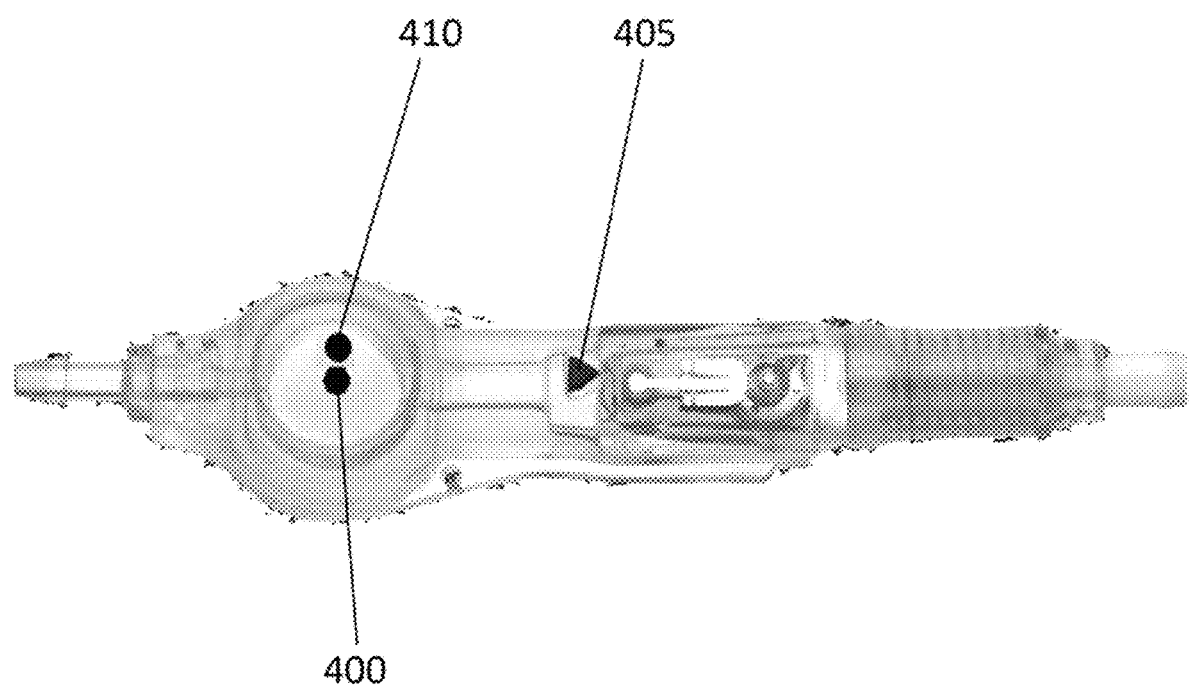
FIG. 17 is a top view of the implantable programmable valve illustrating the first and second fixed magnets and direction of flow arrow.

Referring to FIG. 17, a first fixed, stationary, non-moveable magnet or direction of fluid flow magnet 400 disposed a predetermined distance from the moveable reference marker position may also be included with the implantable valve. That is, the first fixed stationary, non-moveable magnet 400 is disposed a sufficient distance relative to the moveable reference marker position to differentiate the corresponding two markers produced or detected in the magnetic field pattern. The first fixed, stationary, non-moveable magnet 400 produces using the two-dimensional array of 3-axis magnetoresistive sensors a corresponding first fixed magnetic reference marker or direction of fluid flow marker (M').

Prior to the implantable valve device and hence the rotor being set to a specific pressure setting, a line intersecting the central point of the moveable magnetic reference marker (M) and the first fixed magnetic reference marker (M') both are substantially aligned with a direction of flow of bodily fluid (e.g., CSF fluid) line (as denoted by the dashed line in FIGS. 10C & 10D) as marked on the implantable valve device by the arrow 405 in FIG. 17. Once the implantable valve device has been programmed to a specific pressure setting, the direction of the detection device (yaw) may be determined by connecting a line between the moveable reference marker (M) and the first fixed magnetic reference marker (M') relative to the direction of flow line. Furthermore, pitch may be determined based on the detected linear distance between or difference in field strength detected at the two points (e.g., the moveable reference marker (M) and the first fixed magnetic reference marker (M').

Depending on where in the body the device is implanted, inversion of the implantable device over time is possible. As an example, in lumboperitoneal placement of the implantable valve under fascia in the abdominal region of the patient there is an increased risk of inversion of the implantable device. Complete or total inversion (e.g., approximately 180° toll rotation) of the implantable valve device may be identified depending on the detected polarity of the first fixed stationary, non-moveable magnet as either North or South. By way of illustrative example, if the first fixed stationary, non-moveable magnet is disposed within the implantable valve device with its North pole facing upward, then complete or total inversion of the implantable valve may be identified if the detected polarity of the first fixed stationary, non-moveable magnet is South. Alternatively, if the first fixed stationary, non-moveable magnet is disposed within the implantable valve device with its South pole facing upward, then complete or total inversion of the implantable valve may be identified if the detected polarity of the first fixed stationary, non-moveable magnet is North.

It is possible that the implantable valve device may be rotated (roll) by an angle less than that of complete or total inversion (i.e., at an angle between parallel and, perpendicular). Determining possible rotation based solely on detection of the polarity (N or S) of the moveable reference marker (M) fails to take into consideration or compensate for possible roll of the implantable valve device at an angle between parallel and perpendicular. Without ascertaining the precise magnitude of potential roll of the implantable valve device with relation to the locating device, any indication of current setting and/or change in parameters when programming the implantable valve device may be inaccurate causing potentially harmful, at worst life threatening, results. Heretofore, no such precise verification procedure or system exists for detecting the specific angle or degree to which the implantable valve device is rolled. Instead, rotation was imprecisely detected based only on manual touch or manipulation by the technician, nurse or doctor to locate of the implanted device.

Neither manual manipulation nor x-ray imaging is used in accordance with the present invention to detect the specific amount, level, degree or angle of roll of the implantable valve device. Instead, a supplemental or second fixed, stationary, non-moveable magnet 410 (FIG. 17) associated with the implantable valve device produces in the magnetic field pattern a supplemental or second fixed magnetic reference marker (M") used to ascertain the specific degree or angle to which the implantable valve device is rolled. This supplemental or second fixed, stationary, non-movable magnet 410 is displaced laterally to the right or left of the direction of flow of fluid line by a predetermined distance (L) relative to that of the fixed, stationary, non-moveable magnet. It is this supplemental or second fixed, stationary, non-moveable magnet that is used to determine the specific degree or angle of roll of the implanted device and hence roll of its associated rotor 372 with increased accuracy compared to detecting polarity using, only the first fixed magnetic reference marker (in which only total, or complete inversion of the implantable valve device is detectable).

Specifically, the specific level, degree or angle of roll of the implantable medical device is determined based on at least one of: (i) the distance between the two fixed magnetic reference markers (M', M"); (ii) the strength of the first fixed magnet versus that of the strength of the second fixed magnet; and/or (iii) the pattern of the detected magnetic field. For instance, if the two fixed magnets are sufficiently separated, then roll of the implantable medical device will produce a magnetic field pattern by the two dimensional array of 3-axis magnetoresistive sensors that show the second fixed reference marker (M") to the left hand side relative to that of the direction of flow line through which the first fixed magnetic reference marker (M') intersects. Whereas, if the implantable medical device is not rolled, then the magnetic field pattern produced by the two dimensional array of 3-axis magnetoresistive sensors in the indicator device will show the supplemental fixed magnetic reference marker (M") to the right hand side of the direction of flow line through which the fixed magnetic reference marker (M') intersects. However, if the two fixed magnets are closer in proximity, then a blended magnetic field is generated that with additional pattern recognition determine the amount or level of roll.

Once the specific amount, degree, level or angle or roll, if any, of the implantable medical device has been ascertained, appropriate compensation for the specific amount of roll may be taken into consideration when verifying the current settings and/or modifying the parameter settings of the implantable device. For instance, the software upon detecting the specific amount, degree, level or angle or roll may analyze the magnetic fields using an algorithm optimized for rolled polarities. It is the identification of the specific amount, degree, level or angle of roll, if any, of the implantable device in accordance with the present invention using two fixed magnetic reference markers, rather than relying only on hand manipulation or touch, that allows for such compensation or correction.

Referring once again to FIG. 3, below rotor 372 there are fixed in place four stator elements 378 each made of a material that is magnetically soft and permeable, and that is resistant to corrosion in the presence of cerebrospinal fluid, which contains chlorides. Preferred materials include magnetic stainless steel alloys and alloys of nickel, iron, and, molybdenum or cobalt. The stator elements are embedded in a plastic member 380, which is fixed to plate 324 by means of shaft 376. The stator elements are shaped so that the portion of each lying beneath the rotor preferably matches the size of permanent magnets 374. The portions of the stator elements lying radially beyond the rotor are preferably sized to match the area beneath the rotor so that the boundary between poles, when the stator is magnetized, is at the perimeter of the rotor.

In operation the shunt valve assembly is surgically implanted in a patient following well-known procedures. Before implantation the pressure of adjustable valve 314 can be set to the desired level according to the circumstances of the case.

Figure 12:
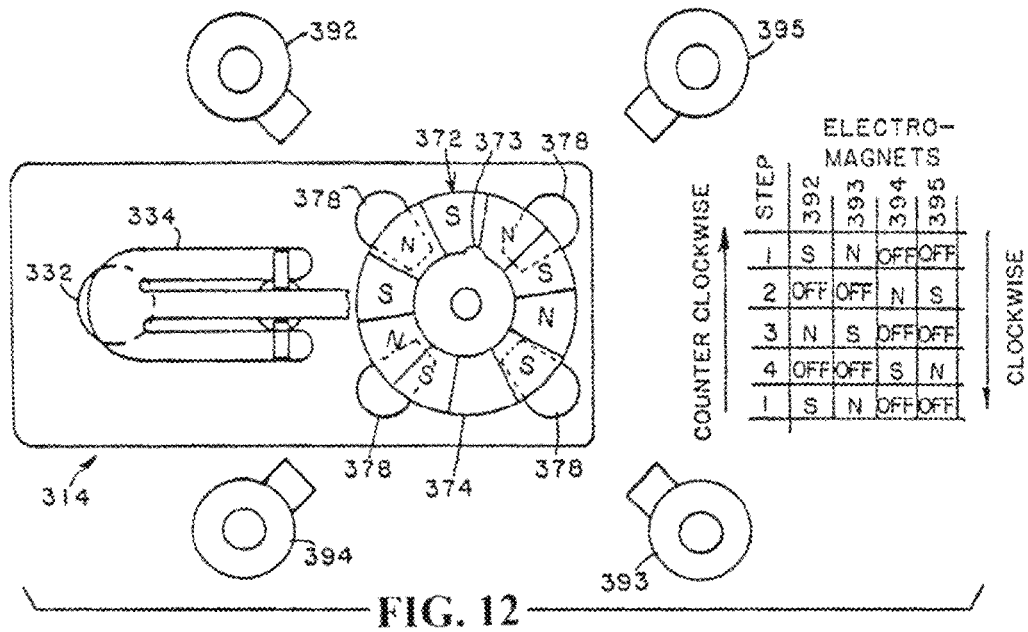
FIG. 12 is a diagrammatic view of the implantable programmable valve being programmed by the external valve adjustment device in which the positions of the external adjusting electromagnets are shown.
Figure 14:
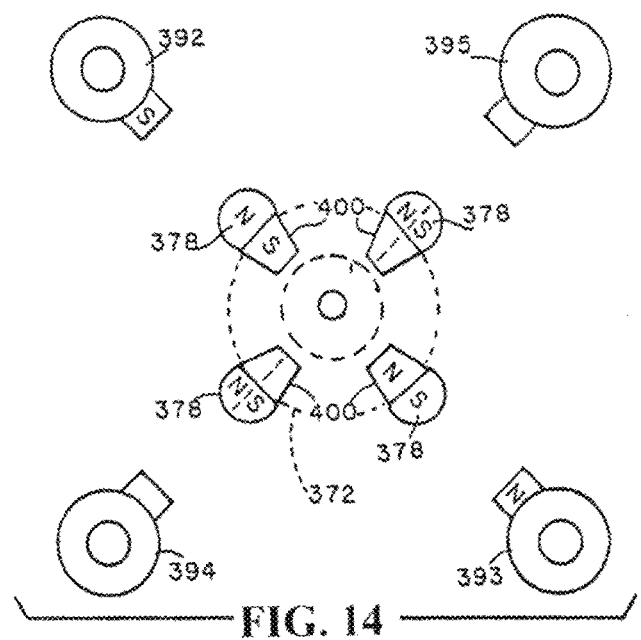
FIG. 14 is a diagrammatic view similar to FIG. 13 except that the rotor and cam has been removed to show the magnetic polarization of the four stator elements.

Valve pressure adjustments are made by applying a pulsed magnetic field to the vicinity of the shunt valve as shown diagrammatically in FIGS. 12-14. A valve adjustment element 390 is applied over adjustable valve 314 in the orientation shown. The valve adjustment element 390 has four electromagnets 392, 393, 394, 395, which are separately controlled by an external control device, shown diagrammatically at 396. Adjustment element 390 has a marking (such as an arrow pointing in the direction of CSF flow) on its exterior to assure that it is applied to the valve in the correct orientation, and it has a groove 398 in its bottom surface sized to fit over the protrusion in the scalp, at the site of the implanted valve. The groove is narrowed at one end 399 to enable correct longitudinal alignment relative to the adjustable valve 314.

The pressure setting of the spring in the inlet valve unit is noninvasively adjusted, by the use of an external programmer or control device 396 having input keys, which the operator uses to select one of a plurality of incremental pressure settings (for example, 18 incremental pressure settings ranging from 20 mm to 190 mm $H_2O$) (196 to 1960 Pa) in 10 mm (98 Pa) increments and a pressure display.

Each of electromagnets 392, 393, 394, 395 can be energized to have either the north or south polarity facing the stator elements, or each can remain off altogether. Movement of rotor 372, in the desired direction and through the desired angle, is achieved by energizing the electromagnets in the sequence shown in the table in FIG. 12. For example, clockwise motion is achieved by first energizing electromagnets 392, 393 to south and north polarities, respectively, and leaving electromagnets 394, 395 off. In the next step electromagnets 392, 393 are left off, and electromagnets 394, 395 are energized to north and south polarities, respectively. The sequence repeats itself after the fourth step. Rotor 372 is shown in FIG. 12 in the position reached after the first step (the polarities of the rotor magnets are those on the bottom surface). If the magnetic field provided by the electromagnets is described by a vector pointing from the south to the north pole of the energized magnets, then it can be seen that the sequence prescribed for causing rotor 372 to rotate clockwise (down the table in FIG. 12) amounts to rotating the field vector in the counterclockwise direction (opposite that of the rotor), in 90 degree steps or increments.

Electromagnets 392, 393, 394, 395 are positioned 90 degrees, apart and spaced equal radial distances from a central axis. When adjustment device 390 is installed properly over valve 314, the central axis of the electromagnets is coincident with the axis of rotation of rotor 372, and each electromagnet is aligned at the same angular position as one stator element 378. It is not, however, necessary that this alignment be exact. The invention is tolerant of alignment errors, which are unavoidable owing to the inability of the user to see rotor 372 or stator elements 378 and to the small size of those elements relative to the size of the external electromagnets.

The magnetic polarization induced in the stator elements 378 as the result of energizing the electromagnets is diagrammatically illustrated in FIG. 14. The two stator elements along the axis connecting the two energized electromagnets are polarized in the radial direction, so that the boundary between the poles lies roughly at the peripheral edge of disk rotor 372. The radially inner portions of these two stator elements, the portions lying beneath rotor 372, have the opposite polarity of the portions lying outside. By contrast, the stator elements along the other axis are polarized so that the boundary between poles lies along the radial direction. Both poles extend beneath the rotor 372. This pattern of polarization will result even if there is substantial error in the orientation of the electromagnets.

Movement of rotor 372 is influenced predominantly by the stator regions 400 (shown FIG. 14) lying beneath the rotor, as it is those portions that are closest to the permanent magnets 374 of the rotor. Accordingly, the part of the stator elements with uniform polarity dominate over those with split polarity. This phenomenon could be emphasized by making the stator elements of a magnetically anisotropic material so that the magnetization induced by the external electromagnets is strongest along the radial axis of the corresponding stator elements.

The number of magnetic poles 374 is selected so that when one pair of radially opposite stator elements 378 is aligned with one pair of magnetic poles 374 (as are the upper left and lower right stator elements in FIG. 12) the other two stator elements (the upper right and lower left in FIG. 12) are each staggered halfway between two of the poles 374. In operation, control device 396 energizes the electromagnets closest to the pair of stators staggered between two magnets, thereby causing the rotor to move through an angle corresponding to one half the width of a magnetic pole 374.

In the exemplary embodiment depicted in FIG. 10B there are ten magnetic poles on each side of the disk, and thus twenty angular increments in one full revolution (i.e., each step is one twentieth of 360 degrees, or 16 degrees). In this exemplary embodiment, only eighteen of these increments are used, corresponding to the eighteen dented steps along the staircase surface of cam 368 (the other two increments are occupied by the detent wall 370 of the cam).

After a pressure is prescribed on control device 396, an enter key is pressed. That initiates a sequence of eighteen steps in the direction of lower pressure settings, counterclockwise rotation of rotor 372. This assures that the cam is returned to a position wherein spring arm 364 is at the lowest step on the cam staircase. If fewer than eighteen steps are actually needed to bring the cam to this position (as will most often be the case), the detent wall provided by element 370 of the cam prevents further rotation. After the eighteen-step resetting sequence is complete, the rotor is moved clockwise by the number of steps corresponding to the prescribed pressure.

The indicator device in accordance with the present invention may be used to assess the magnetic field pattern to verify a current setting of the implantable valve device standalone indication). Moreover, the indicator device may also be used to assess the magnetic field pattern during programming to confirm successful adjustment to the intended setting only. In this programming mode, the fixed magnetic reference marker (M') or direction of flow magnetic reference marker may serve as a "home" marker to confirm that the implantable valve is at its starting position before cycling/rotating to a desired valve pressure setting as well as confirm a final valve pressure setting by ascertaining the degree of rotation of the rotor relative to this home position.

The size and shape of the magnetoresistive sensor array is directly related to the amount of yaw, pitch, and roll that the array is able to detect. In the example illustrated in FIG. 15, the array is rectangular, which allows for more offset within the direction of flow but less yaw. That is, if the indicator device is placed over the implantable programmable valve 90° from the actual direction of flow, the indicator device would not detect the first fixed, stationary, non-moveable (direction of flow) magnet. A circular pattern is preferred and could also be used, but the concern with current technology is spacing of the moveable magnetic reference marker position from the first fixed, stationary, non-moveable magnet versus the size of the sensor array and the ability to detect both. In the example illustrated in FIG. 15, the distance between the center of the moveable magnetic reference marker position (larger dot 1505) and the first fixed, stationary, non-moveable magnet (smaller dot 1515) is 17.5 mm. A distance of 25.95 mm is an estimated projection of how much farther the first fixed, stationary, non-moveable magnet may appear with reasonable levels of pitch (from user or from skull curvature). The smaller square-shape array 1500 would be acceptable if only detecting the moveable reference marker associated with the rotating magnet assembly. The supplemental larger addition 1510 added to the square array to create a rectangular shape array allows for additional detection within direction of flow for the first and second fixed magnets. The outer dimensions are not critical, just representative of the size of an example enclosure.

Figure 16A:
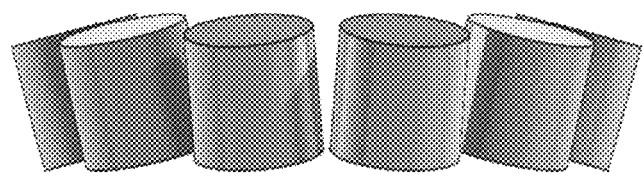
FIGS. 16A & B are exemplary respective side and top views of the permanent-magnet rotor disk comprising a ring of magnets angled outward in a non-parallel arrangement in accordance with the present invention.
Figure 16B:
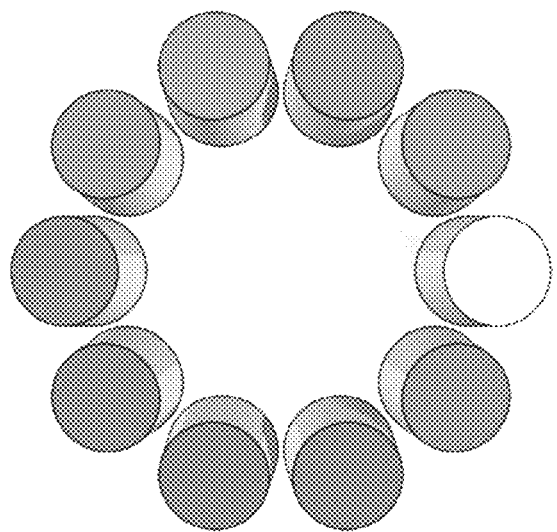

During magnetic resonance imaging, current setting of the implantable programmable valve device may undesirably vary or change. Heretofore, in the CHPV device the plurality of magnets associated with the rotor 372 were disposed perpendicular to the base plate and hence all parallel to one another. As a result, such parallel configuration left the system susceptible to possible knockdown in the presence of MRI. To resist such MR setting changes by the magnets may be configured in an anti-parallel condition. In this regard, referring to FIGS. 16A & B, the plurality of magnets arranged in a ring associated with the rotor 372 may be disposed so as to angle outward whereby no two magnets in the ring are parallel to one another. By angling the magnets in such fashion, the implantable valve will be more robust to possible knockdown in the presence of MRI since no two magnets are parallel to one another at any given time.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A system for detecting spatial location as well as rotation including pitch, roll and yaw of an implantable programmable valve device having a direction of flow of fluid therethrough, the system comprising:
a permanent-magnet rotor disk associated with the implantable programmable valve and having a plurality of three or more magnets arranged in a ring; wherein a single position within the ring represents a moveable reference marker position; wherein the implantable programmable valve further comprises a first fixed, stationary, non-moveable magnet associated with the implantable programmable valve and disposed a predetermined distance relative to the moveable reference marker position;
a two-dimensional array of 3-axis magnetoresistive sensors for producing an asymmetric magnetic field pattern including a moveable reference marker corresponding to the moveable reference marker position in the ring and a first fixed reference marker corresponding to the first fixed, stationary, non-moveable magnet; and
an indicator device for determining: (i) the spatial location of the implantable programmable valve based only on the moveable reference marker; and (ii) the yaw based on the moveable reference marker relative to the first fixed reference marker.

2. The system in accordance with claim 1, wherein total inversion of the implantable medical device is determined based only on a detected polarity of the first fixed, stationary, non-moveable magnet.

3. The system in accordance with claim 1, wherein the plurality of magnets arranged in the ring are an odd number of magnets equal in size and strength; the moveable reference marker position within the ring of plural magnets corresponds to where a single magnetic pole is missing or omitted from the ring; the single magnetic pole that is missing or omitted leaving only a single predetermined spacing displacement (D) between two adjacent magnetic poles identical in polarity; and wherein all remaining adjacent magnetic poles in the ring alternate in polarity and are positioned relative to one another by a substantially equidistant spacing displacement (d), wherein the distance (d) is less than the distance (D).

4. The system in accordance with claim 3, wherein the moveable reference marker is established by the produced asymmetrical magnetic field pattern associated with the moveable reference marker position in the ring due to the missing or omitted single magnetic pole.

5. The system in accordance with claim 1, wherein the plurality of magnets arranged in the ring are an even number of magnets alternating in polarity; the moveable reference marker position associated with the rotor is denoted by a position of only one of the magnets reduced or enlarged in at least one of size and strength relative to all remaining magnets each substantially equal in at least one of size and strength.

6. The system in accordance with claim 1, wherein the plurality of magnets arranged in the ring are an even number of magnets; the moveable reference marker position associated with the rotor is denoted by a position of only one of the magnets in the ring that is rotated by 90 degrees relative to that of all remaining magnets in the ring so that magnetic flux lines produce a more discernible peak.

7. The system in accordance with claim 1, wherein the implantable programmable valve further comprises a second fixed, stationary, non-moveable magnet to ascertain whether the implantable medical device is inverted; depending on whether the produced asymmetrical magnetic field pattern shows a second fixed reference marker corresponding to the second fixed, stationary, non-moveable magnet displaced laterally to right or left of the direction of flow of fluid line by a predetermined distance relative to that of the first fixed reference marker corresponding to the first fixed, stationary, non-moveable magnet.

8. The system in accordance with claim 1, wherein the ring of magnets are angled outward in a non-parallel arrangement.

9. A method for using a system for detecting spatial location as well as rotation including pitch, roll and yaw of an implantable programmable valve device having a direction of flow of fluid therethrough; the system including a permanent-magnet rotor disk associated with the implantable programmable valve and having a plurality of three or more magnets arranged in a ring; wherein a single position within the ring represents a moveable reference marker position; the implantable programmable valve further comprises a first fixed, stationary, non-moveable magnet disposed a predetermined distance relative to the moveable reference marker position; the method comprising the steps of:
selecting a single position from within the ring as the moveable reference marker position;
producing an asymmetrical magnetic field pattern using a two dimensional array of 3-axis magnetoresistive sensors, wherein the asymmetrical magnetic field pattern includes a moveable reference marker corresponding to the moveable reference marker position among the plural magnets in the ring and a first fixed reference marker corresponding to the first fixed, stationary, non-moveable magnet; and
determining using an indicator device: (i) the spatial location of the implantable programmable valve based only on the moveable reference marker; and (ii) the yaw based only on the moveable reference marker relative to the first fixed reference marker.

10. The method in accordance with claim 9, wherein the determining step comprises the steps of:
substantially aligning a line intersecting a central point of the moveable reference marker and the first fixed reference marker with that of the direction of flow of fluid line as denoted on the implantable programmable valve device; and
programming a specific pressure setting using the implantable programmable valve device.

11. The method in accordance with claim 10, wherein the determining step comprises, after the implantable programmable valve device has been programmed to a specific pressure setting, the step of determining the yaw by connecting a line between the moveable reference marker and the first fixed reference marker relative to the direction of flow of fluid line.

12. The method in accordance with claim 11, further comprising the step of determining the pitch based on a detected linear distance between or difference in field strength detected at the moveable reference marker and the first fixed reference marker.

13. The method in accordance with claim 9, wherein total inversion of the implantable medical device is determined based only on a detected polarity of the first fixed, stationary, non-moveable magnet.

14. The method in accordance with claim 9, wherein the implantable programmable valve device further includes a second fixed, stationary, non-moveable magnet displaced laterally to the right or left of the direction of flow line by a predetermined distance relative to that of the fixed magnet; wherein the magnetic field pattern produced using the two dimensional array of 3-axis magnetoresistive sensors includes a second fixed reference marker corresponding to the second fixed, stationary, non-moveable magnet; the method further comprising the steps of:
 determining a specific amount to which the implantable programmable valve is rolled based on at least one of: (i) a distance between the first and second fixed reference markers; (ii) a strength of the first fixed, stationary, non-moveable magnet relative to that of a strength of the second fixed, stationary, non-moveable magnet; and/or (iii) a pattern of the magnetic field produced by the two-dimensional array of 3-axis magnetoresistive sensors.

15. The method in accordance with claim 9, wherein the plurality of magnets arranged in the ring are an odd number of magnets equal in size and strength; the moveable reference marker position within the ring of plural magnets corresponds to where a single magnetic pole is missing or omitted from the ring; the single magnetic pole that is missing or omitted leaving only a single predetermined spacing displacement (D) between two adjacent magnetic poles identical in polarity; and wherein all remaining adjacent magnetic poles in the ring alternate in polarity and are positioned relative to one another by a substantially equidistant spacing displacement (d), wherein the distance (d) is less than the distance (D).

16. The method in accordance with claim 9, wherein the plurality of magnets arranged in the ring are an even number of magnets alternating in polarity; the moveable reference marker position associated with the rotor is denoted by a position of only one of the magnets reduced or enlarged in at least one of size and strength relative to all remaining magnets each substantially equal in at least one of size and strength.

17. The method in accordance with claim 9, wherein the plurality of magnets arranged in the ring are an even number of magnets; the moveable reference marker position associated with the rotor is denoted by a position of only one of the magnets in the ring that is rotated by 90 degrees relative to that of all remaining magnets in the ring so that magnetic flux lines produce a more discernible peak.

18. The method in accordance with claim 9, wherein the ring of magnets are angled outward in a non-parallel arrangement.

* * * * *